US007022661B2

United States Patent
Behler et al.

(10) Patent No.: US 7,022,661 B2
(45) Date of Patent: Apr. 4, 2006

(54) ALKYL-AND/OR ALKYLENE OLIGOGLYCOSIDE BETAINE ESTER QUATERNARIES

(75) Inventors: Ansgar Behler, Bottrop (DE); Frank Clasen, Hilden (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 41 days.

(21) Appl. No.: 10/501,490

(22) PCT Filed: Jan. 7, 2003

(86) PCT No.: PCT/EP03/00062

§ 371 (c)(1),
(2), (4) Date: Jul. 14, 2004

(87) PCT Pub. No.: WO03/059298

PCT Pub. Date: Jul. 24, 2003

(65) Prior Publication Data

US 2005/0054551 A1    Mar. 10, 2005

(30) Foreign Application Priority Data

Jan. 16, 2002    (DE) ................. 102 01 354

(51) Int. Cl.
  *C11D 1/90*    (2006.01)
  *C11D 3/22*    (2006.01)
  *C07H 15/00*   (2006.01)

(52) U.S. Cl. .......... 510/470; 510/433; 510/471; 510/474; 510/504; 424/70.13; 536/1.11; 536/123.1; 536/17.2; 536/18.7

(58) Field of Classification Search ............ 510/433, 510/470, 471, 474, 504; 424/70.13; 536/1.11, 536/123.1, 17.2, 18.7
See application file for complete search history.

(56) References Cited

U.S. PATENT DOCUMENTS

2004/0037794 A1    2/2004   Deblef

FOREIGN PATENT DOCUMENTS

| DE | 199 17 745 |   | 3/2000 |
|----|------------|---|--------|
| EP | WO 00/15669 | * | 3/2000 |
| WO | WO 02/07684 |   | 1/2002 |

OTHER PUBLICATIONS

Biermann et al., "Alklpolyglucoside—Technologie und Eigenschaften," Starch/Staerke, vol. 45, 1993, pp. 281, 284-288.
Barry Salka, "Alkyl Polyglycosides," Cosmetics & Toiletries, vol. 108, 1993, pp. 89-94, Mar. 1993.
Kahre et al., "Alkylpolyglycoside—Ein neues Konzept für Pflege und Verträglichkeit in der Kosmetik," SÖFW Journal, vol. 121, 1995, pp. 598, 600-601, 604-611.

* cited by examiner

*Primary Examiner*—Brian P. Mruk
(74) *Attorney, Agent, or Firm*—John F. Daniels; Daniel S. Ortiz

(57) ABSTRACT

A composition containing an alk(en)yl oligoglycoside betaine esterquat corresponding to formula I:

$$R^1O(G)_nOCOCR^2R^3NR^4R^5R^6 \qquad (I)$$

wherein $R^1$ is an alk(en)yl group having from about 4 to about 22 carbon atoms, G is a sugar unit containing 5 or 6 carbon atoms and n is a number from 1 to about 10, $R^2$ is H or a $CH_3$ group, $R^3$ is H or a linear and/or branched alk(en)yl group having from 1 to about 6 carbon atoms, $R^4$, $R^5$ and $R^6$, independently of one another, represent a linear and/or branched alk(en)yl group having from 1 to about 24 carbon atoms or a linear and/or branched hydroxyalk(en)yl group having from 1 to about 24 carbon atoms.

12 Claims, No Drawings

US 7,022,661 B2

ALKYL-AND/OR ALKYLENE OLIGOGLYCOSIDE BETAINE ESTER QUATERNARIES

BACKGROUND OF THE INVENTION

This application is a 371 of PCT/EP03/00062 filed Jan. 7, 2003.

FIELD OF THE INVENTION

This invention relates to alk(en)yl oligoglycoside betaine esterquats, to a process for their production and to their use as emulsifiers, hair conditioners and fabric softeners.

By virtue of their excellent ecotoxicological properties, cationic surfactants, such as esterquats for example, are acquiring increasing significance both in regard to fabric softeners and for cosmetic applications. In cosmetic preparations, they may be present both in emulsions and lotions for skin care and in surface-active preparations, such as for example shampoos, shower baths, rinses, conditioners and the like, for hair care. There is still a need on the market for new cationic surfactants which can be obtained from natural raw material sources and which are highly hydrophilic by comparison with compounds made up solely of alkyl chains (for example cetyl trimethyl ammonium chloride). This relatively high hydrophilia should not be obtained by the introduction of alkoxide groups in order inter alia to reduce environmental pollution to a relatively low level.

Accordingly, the problem addressed by the present invention was to provide new cationic surfactants, which could be produced from a natural raw material source, would be free from ethylene and/or propylene oxide and would therefore cause relatively little environmental pollution, and a process for their production.

DESCRIPTION OF THE INVENTION

The present invention relates to alk(en)yl oligoglycoside betaine esterquats corresponding to formula (I):

$$R^1O(G)_nOCOCR^2R^3NR^4R^5R^6 \qquad (I)$$

in which $R^1$ is an alk(en)yl group containing 4 to 22 carbon atoms, G is a sugar unit containing 5 or 6 carbon atoms and n is a number of 1 to 10, $R^2$ is H or a $CH_3$ group, $R^3$ is H or a linear and/or branched alk(en)yl group containing 1 to 6 carbon atoms, $R^4$, $R^5$ and $R^6$ independently of one another represent a linear and/or branched alk(en)yl group containing 1 to 24 carbon atoms or a linear and/or branched hydroxyalk(en)yl group containing 1 to 24 carbon atoms.

The present invention also relates to a process for the production of alk(en)yl oligoglycoside betaine esterquats, in which alk(en)yl oligoglycosides corresponding to formula (II):

$$R^1O(G)_n \qquad (II)$$

in which $R^1$ is an alk(en)yl group containing 4 to 22 carbon atoms, G is a sugar unit containing 5 or 6 carbon atoms and n is a number of 1 to 10, are reacted with an α-halocarboxylic acid corresponding to formula (III):

$$XCR^2R^3COOH \qquad (III)$$

in which $R^2$ is H or a $CH_3$ group, $R^3$ is H or a linear and/or branched alk(en)yl group containing 1 to 6 carbon atoms and X is halogen, and then with tertiary amines corresponding to formula (IV):

$$NR^4R^5R^6 \qquad (IV)$$

in which $R^4$, $R^5$ and $R^6$ independently of one another represent a linear and/or branched alk(en)yl group containing 1 to 24 carbon atoms or a linear and/or branched hydroxyalkyl and/or hydroxyalkenyl group containing 1 to 24 carbon atoms.

It has surprisingly been found that alk(en)yl oligoglycoside betaine esterquats, as new cationic sugar surfactants, can be produced by reacting alk(en)yl oligoglycosides with α-halocarboxylic acid and tertiary amines. It is of particular advantage that these new surfactants emanate from a natural raw material source, are free from ethylene and/or propylene oxide and hence pose relatively little threat to the environment. In addition, the new cationic surfactants should be highly hydrophilic. Also, these compounds are suitable as conditioners for the hair (hair rinses) and for fabrics (fabric softeners).

Alk(en)yl Oligoglycoside Betaine Esterquats

The present invention relates to alk(en)yl oligoglycoside betaine esterquats [alk(en)yl=alkyl and/or alkenyl] corresponding to formula (I):

$$R^1O(G)_nOCOCR^2R^3NR^4R^5R^6 \qquad (I)$$

in which $R^1$ is an alk(en)yl group containing 4 to 22 carbon atoms, G is a sugar unit containing 5 or 6 carbon atoms and n is a number of 1 to 10, $R^2$ is H or a $CH_3$ group, $R^3$ is H or a linear and/or branched alk(en)yl group containing 1 to 6 carbon atoms, $R^4$, $R^5$ and $R^6$ independently of one another represent a linear and/or branched alk(en)yl group containing 1 to 24 carbon atoms or a linear and/or branched hydroxyalk(en)yl group containing 1 to 24 carbon atoms.

A preferred embodiment of the invention is characterized by the use of alk(en)yl oligoglycoside betaine esterquats corresponding to formula (I), in which $R^1$ is an alk(en)yl group containing 4 to 22 carbon atoms, G is a sugar unit containing 5 or 6 carbon atoms and n is a number of 1 to 10, $R^2$ and $R^3$ are H or a $CH_3$ group, preferably H, $R^4$ and $R^5$ independently of one another represent a linear and/or branched alk(en)yl group containing 1 to 6 carbon atoms or a linear and/or branched hydroxyalkyl and/or hydroxyalkenyl alkenyl group containing 1 to 6 carbon atoms and preferably a $CH_3$ group or a hydroxyethyl group, $R^6$ is a linear and/or branched alk(en)yl group containing 1 to 24 carbon atoms or a linear and/or branched hydroxyalkyl and/or hydroxyalkenyl group containing 1 to 24 carbon atoms.

Another embodiment of the invention is characterized by the use of alk(en)yl oligoglycoside betaine esterquats corresponding to formula (I), in which $R^1$ is an alk(en)yl group containing 4 to 22 carbon atoms, G is a sugar unit containing 5 or 6 carbon atoms and n is a number of 1 to 10, $R^2$ and $R^3$ are H, $R^4$ and $R^5$ represent a $CH_3$ group or a hydroxyethyl group, $R^6$ is a linear and/or branched alk(en)yl group containing 1 to 24 carbon atoms or a linear and/or branched hydroxyalkyl and/or hydroxyalkenyl group containing 1 to 24 carbon atoms.

The alk(en)yl oligoglycoside betaine esterquats according to the invention are used in surface-active preparations, preferably in laundry detergents, dishwashing detergents and cleaning products, and cosmetic and/or pharmaceutical preparations in quantities of 0.01 to 60% by weight, preferably in quantities of 0.05 to 30% by weight and more particularly in quantities of 2.5 to 20% by weight, based on the active substance content.

Production of Alk(en)yl Glycerol Ether Carboxylic Acids

The alk(en)yl oligoglycoside betaine esterquats are obtained by reaction of alk(en)yl oligoglycosides corresponding to formula (II) with α-halocarboxylic acids corresponding to formula (III) and tertiary amines corresponding to formula (IV). The preferred alk(en)yl oligoglycoside betaine esterquats obtainable by this reaction were mentioned in the previous chapter.

Alkyl and alkenyl oligoglycosides are known nonionic surfactants which correspond to formula (II):

$$R^1O-[G]_n \qquad (II)$$

where $R^1$ is an alk(en)yl group containing 4 to 22 carbon atoms, G is a sugar unit containing 5 or 6 carbon atoms and n is a number of 1 to 10. They may be obtained by the relevant methods of preparative organic chemistry. The overviews presented by Bierman et al. in *Starch/Stärke* 45, 281 (1993), by B. Salka in *Cosm. Toil.* 108, 89 (1993) and by J. Kahre in *SÖFW-Journal No.* 8, 598 (1995) are cited as representative of the extensive literature available on this subject.

The alk(en)yl oligoglycosides may be derived from aldoses or ketoses containing 5 or 6 carbon atoms, preferably glucose. Accordingly, the preferred alk(en)yl oligoglycosides are alk(en)yl oligoglucosides. The index n in general formula (II) indicates the degree of oligomerization (DP), i.e. the distribution of mono- and oligoglycosides, and is a number of 1 to 10. Whereas n in a given compound must always be an integer and, above all, may assume a value of 1 to 6, the value n for a certain alkyl oligoglycoside is an analytically determined calculated quantity which is generally a broken number. Alk(en)yl oligoglycosides having an average degree of oligomerization n of 1.1 to 3.0 are preferably used. Alk(en)yl oligoglycosides having a degree of oligomerization of less than 1.7 and, more particularly, between 1.2 and 1.4 are preferred from the applicational perspective. The alkyl or alkenyl radical $R^1$ may preferably be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl radical $R^1$ may preferably be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

α-Halocarboxylic acids may be obtained by the relevant methods of organic chemistry and correspond to formula (III):

$$XCR^2R^3COOH \qquad (III)$$

in which $R^2$ is H or a $CH_3$ group, $R^3$ is H or a linear and/or branched alk(en)yl group containing 1 to 6 carbon atoms and X is halogen. In one particular embodiment of the invention, $R^2$ and $R^3$ represent H or a $CH_3$ group, more particularly H. More particularly, α-haloacetic acid, for example monochloroacetic acid, is used.

Tertiary amines which may be used for the purposes of the invention correspond to formula (IV):

$$NR^4R^5R^6 \qquad (IV)$$

in which $R^4$, $R^5$ and $R^6$ independently of one another represent a linear and/or branched alk(en)yl group containing 1 to 24 carbon atoms or a linear and/or branched hydroxyalkyl and/or hydroxyalkenyl group containing 1 to 24 carbon atoms. In one particular embodiment of the invention, $R^4$ and $R^5$ independently of one another represent a linear and/or branched alk(en)yl group containing 1 to 6 carbon atoms or a linear and/or branched hydroxyalkyl and/or hydroxyalkenyl group containing 1 to 6 carbon atoms and $R^6$ is a linear and/or branched alk(en)yl group containing 1 to 24 carbon atoms or a linear and/or branched hydroxyalkyl and/or hydroxyalkenyl group containing 1 to 24 carbon atoms. In another embodiment of the invention, $R^4$ and $R^5$ independently of one another represent a $CH_3$ group or a hydroxyethyl group and $R^6$ is a linear and/or branched alk(en)yl group containing 1 to 24 carbon atoms or a linear and/or branched hydroxyalkyl and/or hydroxyalkenyl group containing 1 to 24 carbon atoms, preferably a linear and/or branched alk(en)yl group containing 1 to 24 carbon atoms or a linear and/or branched hydroxyalkyl and/or hydroxyalkenyl group containing 1 to 6 carbon atoms.

Accordingly, the tertiary amine may be derived from short-chain tertiary amines, preferably dimethyl ethanolamine, triethanolamine and methyl diethanolamine, or long-chain amines, preferably dimethyl cocoamine, dimethyl laurylamine and dimethyl tallow amine.

To produce the compounds according to the invention, the alk(en)yl oligoglycoside is dried beforehand to a water content of at most 5% by weight and preferably at most 4% by weight, based on the active substance content of the alk(en)yl oligoglycoside, and then introduced into a reaction vessel for the reaction. The alk(en)yl oligoglycoside is then esterified with the α-halocarboxylic acid in a molar ratio of 1:0.5 to 1:3 and preferably 1:1 to 1:1.5, the reaction being carried out with removal of water over a period of 5 to 13 hours and preferably 7 to 12 hours at a temperature of 100 to 130° C. and preferably 115 to 120° C. and in the presence of up to 50% of an organic solvent, based on the reaction mixture as a whole. The organic solvent used is preferably toluene, benzene or xylene, more particularly toluene. The reaction product obtained is then reacted with a tertiary amine corresponding to formula (IV) in a molar ratio of 1:0.5 to 1:3 and preferably 1:1 to 1:1.5 at a temperature of 70 to 100° C. and preferably 80 to 90° C. Organic solvent is added to the tertiary amine beforehand in such a quantity that the reaction mixture is readily stirrable. The reaction is terminated when the theoretical quantity of inorganic halide released is reached. The reaction times are normally 30 minutes to 3 hours and preferably 50 minutes to 1.5 hours.

Commercial Applications

The alk(en)yl oligoglycoside betaine esterquats according to the invention may be adjusted to any concentration by addition of water; the water content is preferably 20 to 85% by weight, more preferably 20 to 75% by weight and most preferably 50 to 70% by weight.

The alk(en)yl oligoglycoside betaine esterquats may be used as surfactants in surface-active preparations. Surface-active preparations in the context of the invention are preferably understood to be laundry detergents, dishwashing detergents and cleaning products and also cosmetic and/or pharmaceutical preparations, more particularly cosmetic and/or pharmaceutical preparations. More particularly, the products according to the invention may be used in hair conditioners and fabric softeners. These surface-active preparations may contain pearlizing waxes, consistency factors, thickeners, superfatting agents, stabilizers, silicone compounds, fats, waxes, antioxidants, antidandruff agents, swelling agents, tyrosine inhibitors, hydrotropes, solubilizers, preservatives, perfume oils, dyes, other surfactants and other ingredients typical, for example, of laundry detergents, dishwashing detergents and cleaning products as further auxiliaries and additives. Preferred cosmetic and/or pharmaceutical preparations are oral hygiene and dental care preparations, hair shampoos, hair lotions, foam baths, shower baths, creams, lotions, gels, emulsions, wax/fat compounds, stick preparations or ointments. Besides the alk(en)yl oligoglycoside betaine esterquats according to the invention, these surface-active preparations may contain other known ingredients typical of the particular application in the usual concentrations.

The preparations according to the invention show not only conditioning properties [conditioners] for hair (hair rinses) and fabrics (fabric softeners), but also foaming and cleaning properties. In addition, relatively long-chain alk(en)yl oligoglycoside betaine esterquats, such as $C_{16/18}$ oligoglycoside betaine esterquats for example, can have emulsifying properties and may therefore be used in cosmetic and/or pharmaceutical preparations. Accordingly, the present invention also relates to the use of the alk(en)yl oligoglycoside betaine esterquats as hair conditioners, as fabric softeners and as emulsifiers. More particularly, $C_{16/18}$ alkyl oligoglycoside betaine esterquats may be used as emulsifiers in all types of emulsions known to the expert.

Typical cosmetic and/or pharmaceutical cleaning preparations preferably have the following composition, based on the active substance content:
(a) 0.05 to 20, preferably 0.5 to 10 and more particularly 2.5 to 18% by weight alk(en)yl oligoglycoside betaine esterquats,
(b) 0.05 to 15, preferably 0.5 to 10 and more particularly 2.5 to 7.5% by weight betaines and optionally
(c) 0 to 15, preferably 0.5 to 10 and more particularly 2.5 to 7.5% by weight anionic surfactants, with the proviso that the quantities shown add up to 100% by weight with water and optionally other auxiliaries and additives.

Typical liquid laundry/dishwashing detergents and cleaners preferably have the following composition, based on the active substance content:
(a) 2.5 to 30, preferably 7 to 25 and more particularly 10 to 20% by weight alk(en)yl oligoglycoside betaine esterquats,
(b) 0.05 to 15, preferably 0.5 to 10 and more particularly 2.5 to 7.5% by weight betaines and optionally
(c) 2.5 to 30, preferably 7 to 25 and more particularly 10 to 20% by weight anionic surfactants, with the proviso that the quantities shown add up to 100% by weight with water and optionally other auxiliaries and additives.

Typical cosmetic and/or pharmaceutical emulsions preferably have the following composition, based on the active substance content:

(a) 0.05 to 15, preferably 0.5 to 10 and more particularly 1 to 5% by weight alk(en)yl oligoglycoside betaine esterquats, preferably $C_{16/18}$ alkyl oligoglycoside betaine esterquats,
(b) 3 to 30, preferably 5 to 20 and more particularly 7 to 15% by weight oil components and optionally
(c) 0.5 to 20 and preferably 2.5 to 10% by weight consistency factors, with the proviso that the quantities shown add up to 100% by weight with water and optionally other auxiliaries and additives.

EXAMPLES

The following Examples are intended to illustrate the invention without limiting it in any way.

Example 1

(a) Preparation of $C_{12/14}$ Alkyl Oligoglycoside Chloroacetic Acid Ester

In a 1-liter three-necked flask, 61.4 g (0.65 mol) chloroacetic acid were added to 214.0 g (0.5 mol) of a citric-acid-neutralized, freeze-dried $C_{12/14}$ alkyl oligoglycoside (water-free, 1.7% by weight water; based on Plantacare 1200 UP, Cognis) with elimination of water at a temperature of 115–120° C. and in the presence of 250 ml added toluene. The reaction was terminated after 11.25 h. 513.4 g of a dark yellow, cloudy and liquid product were obtained. The alkyl oligoglucoside conversion amounted to 70.6%.

| | |
|---|---|
| acid value: | 19.9 |
| saponification value: | 158.0 |
| free monoglucosides (GC) | 8.1% |
| free diglucosides (GC) | 4.6% |
| free triglucosides (GC) | 0.8% |
| free tetraglucosides (GC) | 0.3% |
| free pentaglucosides (GC) | 0.1% |

(b) Preparation of Cationic $C_{12/14}$ Alkyl Oligoglycoside Betaine Esterquat

In a 500 ml three-necked flask, 29.0 g (0.3 mol) of the $C_{12/14}$ alkyl oligoglycoside chloroacetic acid ester prepared in (a) were reacted with 27.6 g (0.3 mol) N,N-dimethyl ethanolamine at 80° C. in 220 g toluene. The reaction was terminated after 1.25 h when the theoretical quantity of inorganic chloride (2.82%) had been released. The solvent—toluene—was distilled off in vacuo (35 mbar) at 60 to 80° C. in a rotary evaporator. The product was adjusted with water to a concentration of 30% active substance. The product was a dark brown liquid.

(c) Preparation of a Cationic $C_{12/14}$ Alkyl Oligoglucoside Betaine Esterquat Based on N,N-Dimethyl Octyl/Decyl Amine In a 250 ml three-necked flask, 41.5 g (96.7 mmol) of the $C_{12/14}$ APG chloroacetic acid ester prepared in a) were reacted with 17.2 g (96.7 mmol) N,N-dimethyl octyl/decyl amine at 80° C. in 36.7 g toluene. The reaction was terminated after 1 hour 10 minutes when the theoretical quantity of inorganic chloride (4.05%) had been released. After addition of 250 g water, the toluene was distilled off in a water separator for heavy solvents. The pH was then adjusted to 6.4 A yellow, homogeneous liquid product was obtained.

| | |
|---|---|
| cationic surfactant content: | 17.4% |
| dry residue: | 24.0% |

The invention claimed is:

1. A composition comprising an alk(en)yl oligoglycoside betaine esterquat corresponding to formula I:

$$R^1O(G)_nOCOCR^2R^3NR^4R^5R^6 \quad (I)$$

wherein $R^1$ is an alk(en)yl group having from about 4 to about 22 carbon atoms, G is a sugar unit containing 5 or 6 carbon atoms and n is a number from 1 to about 10, $R^2$ is H or a $CH_3$ group, $R^3$ is H or a linear and/or branched alk(en)yl group having from 1 to about 6 carbon atoms, $R^4$, $R^5$ and $R^6$, independently of one another, represent a linear and/or branched alk(en)yl group having from 1 to about 24 carbon atoms or a linear and/or branched hydroxyalk(en)yl group having from 1 to about 24 carbon atoms.

2. The composition of claim 1 wherein the alk(en)yl oligoglycoside betaine is present in the composition in an amount of from about 0.01 to 60% by weight, based on the weight of the composition.

3. The composition of claim 1 wherein the alk(en)yl oligoglycoside betaine is present in the composition in an amount of from about 0.05 to 30% by weight, based on the weight of the composition.

4. The composition of claim 1 wherein the alk(en)yl oligoglycoside betaine is present in the composition in an amount of from about 2.5 to 20% by weight, based on the weight of the composition.

5. The composition of claim 1 wherein in formula I, $R^2$ and $R^3$ are H, $R^4$ and $R^5$ represent a methyl group or a hydroxyethyl group.

6. The composition of claim 1 further comprising a co-surfactant selected from the group consisting of a betaine, an anionic surfactant, and mixtures thereof.

7. A process for making an alk(en)yl oligoglycoside betaine esterquat comprising:
 (a) providing an alk(en)yl oligoglycoside corresponding to formula (II):

$$R^1O(G)_n \quad (II)$$

wherein $R^1$ is an alk(en)yl group having from about 4 to 22 carbon atoms, G is a sugar unit containing 5 or 6 carbon atoms and n is a number of 1 to 10;
 (b) providing an α-halocarboxylic acid corresponding to formula (III):

$$XCR^2R^3COOH \quad (III)$$

wherein $R^2$ is H or a $CH_3$ group, $R^3$ is H or a linear and/or branched alk(en)yl group having from 1 to about 6 carbon atoms and X is a halogen;
 (c) reacting (a) and (b) to form a reaction product;
 (d) providing a tertiary amines corresponding to formula (IV):

$$NR^4R^5R^6 \quad (IV)$$

wherein $R^4$, $R^5$ and $R^6$, independently of one another, represent a linear and/or branched alk(en)yl group having from 1 to about 24 carbon atoms or a linear and/or branched hydroxyalkyl and/or hydroxyalkenyl group having from 1 to about 24 carbon atoms; and
 (e) reacting the reaction product of (c) with (d) to form the alk(en)yl oligoglycoside betaine.

8. The process of claim 7 wherein the alk(en)yl oligoglycoside of (a) has a water content of up to 5% by weight.

9. The process of claim 7 wherein the alk(en)yl oligoglycoside of (a) and the α-halocarboxylic acid of (b) are reacted in a molar ratio of from about 1:0.5 to 1:3.

10. The process of claim 7 wherein the alk(en)yl oligoglycoside of (a) and the α-halocarboxylic acid of (b) are reacted in a molar ratio of from about 1:1 to 1:1.5.

11. The process of claim 7 wherein the reaction product of (c) and the tertiary amine of (d) are reacted in a molar ratio of from about 1:0.5 to 1:3.

12. The process of claim 7 wherein the reaction product of (c) and the tertiary amine of (d) are reacted in a molar ratio of from about 1:1 to 1:1.5.

* * * * *